US008865468B2

(12) United States Patent
Kilian et al.

(10) Patent No.: US 8,865,468 B2
(45) Date of Patent: *Oct. 21, 2014

(54) HOMOLOGOUS RECOMBINATION IN AN ALGAL NUCLEAR GENOME

(75) Inventors: Oliver Kilian, Alameda, CA (US); Bertrand Vick, Emeryville, CA (US)

(73) Assignee: Aurora Algae, Inc., Hayward, CA (US)

( * ) Notice: Subject to any disclaimer, the term of this patent is extended or adjusted under 35 U.S.C. 154(b) by 414 days.

This patent is subject to a terminal disclaimer.

(21) Appl. No.: 12/581,812

(22) Filed: Oct. 19, 2009

(65) Prior Publication Data

US 2011/0091977 A1 Apr. 21, 2011

(51) Int. Cl.
*C12N 15/79* (2006.01)
*C12N 1/13* (2006.01)

(52) U.S. Cl.
CPC .................... *C12N 15/79* (2013.01)
USPC .................... 435/471; 435/257.1

(58) Field of Classification Search
None
See application file for complete search history.

(56) References Cited

U.S. PATENT DOCUMENTS

| | | | |
|---|---|---|---|
| 1,926,780 | A | 9/1933 | Lippincott |
| 3,468,057 | A | 9/1969 | Buisson et al. |
| 3,962,466 | A | 6/1976 | Nakabayashi |
| 4,003,337 | A | 1/1977 | Moore |
| 4,267,038 | A | 5/1981 | Thompson |
| 4,365,938 | A | 12/1982 | Warinner |
| 4,535,060 | A | 8/1985 | Comai |
| 4,658,757 | A | 4/1987 | Cook |
| 5,105,085 | A | 4/1992 | McGuire et al. |
| 5,478,208 | A | 12/1995 | Kasai et al. |
| 5,527,456 | A | 6/1996 | Jensen |
| 5,661,017 | A | 8/1997 | Dunahay et al. |
| 5,668,298 | A | 9/1997 | Waldron |
| 5,723,595 | A | 3/1998 | Thompson et al. |
| 5,823,781 | A | 10/1998 | Hitchcock et al. |
| 6,027,900 | A | 2/2000 | Allnutt et al. |
| 6,117,313 | A | 9/2000 | Goldman et al. |
| 6,143,562 | A | 11/2000 | Trulson et al. |
| 6,166,231 | A | 12/2000 | Hoeksema |
| 6,297,054 | B1 | 10/2001 | Maliga et al. |
| 6,372,460 | B1 | 4/2002 | Gladue et al. |
| 6,448,055 | B1 | 9/2002 | Shimizu et al. |
| 6,736,572 | B2 | 5/2004 | Geraghty |
| 6,750,048 | B2 | 6/2004 | Ruecker et al. |
| 6,831,040 | B1 | 12/2004 | Unkefer et al. |
| 6,871,195 | B2 | 3/2005 | Ryan et al. |
| 7,244,609 | B2 | 7/2007 | Drocourt et al. |
| 7,381,326 | B2 | 6/2008 | Haddas |
| 7,410,637 | B2 | 8/2008 | Sayre et al. |
| 7,449,568 | B2 | 11/2008 | Fukuda et al. |
| 7,547,551 | B2 | 6/2009 | Schuler et al. |
| 8,039,230 | B2 | 10/2011 | Otte et al. |
| 8,119,859 | B2 | 2/2012 | Vick et al. |
| 8,314,228 | B2 | 11/2012 | Kilian et al. |
| 8,318,482 | B2 | 11/2012 | Vick et al. |
| 2003/0049720 | A1 | 3/2003 | Hoshino et al. |
| 2003/0140321 | A1 | 7/2003 | Ryan et al. |
| 2003/0143743 | A1 | 7/2003 | Schuler et al. |
| 2003/0199490 | A1 | 10/2003 | Antoni-Zimmermann et al. |
| 2003/0211089 | A1 | 11/2003 | Sayre et al. |
| 2004/0161364 | A1 | 8/2004 | Carlson |
| 2004/0262219 | A1 | 12/2004 | Jensen |
| 2005/0064577 | A1 | 3/2005 | Berzin |
| 2005/0095569 | A1 | 5/2005 | Franklin |
| 2005/0124010 | A1 | 6/2005 | Short et al. |
| 2005/0170479 | A1 | 8/2005 | Weaver et al. |
| 2005/0181345 | A1 | 8/2005 | Bradbury et al. |
| 2005/0260553 | A1 | 11/2005 | Berzin |
| 2006/0031087 | A1 | 2/2006 | Fox et al. |
| 2006/0044259 | A1 | 3/2006 | Hotelling et al. |
| 2006/0045750 | A1 | 3/2006 | Stiles |
| 2006/0101535 | A1 | 5/2006 | Forster et al. |
| 2006/0122410 | A1 | 6/2006 | Fichtali et al. |
| 2006/0155558 | A1 | 7/2006 | Corpening |
| 2006/0166243 | A1 | 7/2006 | Su et al. |

(Continued)

FOREIGN PATENT DOCUMENTS

| | | |
|---|---|---|
| CN | 1627764 | 6/2005 |
| CN | 1867140 | 11/2006 |
| CN | 1956335 | 5/2007 |
| CN | 101289569 | 10/2008 |
| WO | WO2004/106238 A2 | 12/2001 |
| WO | 2007084078 A1 | 7/2007 |
| WO | WO/2008/060571 A2 | 5/2008 |
| WO | 2008106803 A1 | 9/2008 |
| WO | WO/2008/060571 A3 | 11/2008 |
| WO | WO/2008/060571 A8 | 2/2009 |

(Continued)

OTHER PUBLICATIONS

Prein et al. FEBS Letters 485 (2000) 29-34.*

(Continued)

*Primary Examiner* — Nancy T Vogel
(74) *Attorney, Agent, or Firm* — Carr & Ferrell LLP

(57) ABSTRACT

Exemplary transformation methods are provided for introducing deoxyribonucleic acid (DNA) into the nucleus of an algal cell. A transformation construct may be prepared, with the transformation construct having a first sequence of DNA similar to a corresponding first sequence of nuclear DNA, a second sequence of DNA similar to a corresponding second sequence of the nuclear DNA, and a sequence of DNA of interest inserted between the first and second sequences of DNA of the transformation construct. A target sequence of DNA inserted between the first and second corresponding sequences of the nuclear DNA may be transformed, resulting in replacement of the target sequence of DNA with the sequence of DNA of interest. Also provided are exemplary transformation constructs, with some transformation constructs having a first sequence of DNA similar to a corresponding first sequence of nuclear DNA of an algal cell, a second sequence of DNA similar to a corresponding second sequence of nuclear DNA of the algal cell, and a sequence of DNA of interest inserted between the first and second sequences of the transformation construct.

20 Claims, 5 Drawing Sheets

(56) References Cited

U.S. PATENT DOCUMENTS

| | | | |
|---|---|---|---|
| 2006/0166343 | A1 | 7/2006 | Hankamer et al. |
| 2006/0192690 | A1 | 8/2006 | Philipp |
| 2007/0178451 | A1 | 8/2007 | Deng et al. |
| 2008/0118964 | A1 | 5/2008 | Huntley et al. |
| 2008/0120749 | A1 | 5/2008 | Melis et al. |
| 2008/0160488 | A1 | 7/2008 | Younkes et al. |
| 2008/0160591 | A1 | 7/2008 | Willson et al. |
| 2008/0194029 | A1 | 8/2008 | Hegemann et al. |
| 2008/0268539 | A1 | 10/2008 | Singh et al. |
| 2008/0293132 | A1 | 11/2008 | Goldman et al. |
| 2009/0029445 | A1 | 1/2009 | Eckelberry et al. |
| 2009/0061493 | A1 | 3/2009 | Trimbur et al. |
| 2009/0061928 | A1 | 3/2009 | Lee et al. |
| 2009/0148931 | A1 | 6/2009 | Wilkerson et al. |
| 2009/0234146 | A1 | 9/2009 | Cooney et al. |
| 2009/0317857 | A1 | 12/2009 | Vick et al. |
| 2009/0317878 | A1* | 12/2009 | Champagne et al. ......... 435/134 |
| 2009/0317904 | A1 | 12/2009 | Vick et al. |
| 2009/0319338 | A1 | 12/2009 | Parks et al. |
| 2009/0325270 | A1 | 12/2009 | Vick et al. |
| 2010/0068772 | A1 | 3/2010 | Downey |
| 2010/0100520 | A1 | 4/2010 | Dargue et al. |
| 2010/0198659 | A1 | 8/2010 | Meltzer et al. |
| 2010/0210003 | A1 | 8/2010 | King |
| 2010/0210832 | A1 | 8/2010 | Kilian et al. |
| 2010/0314324 | A1 | 12/2010 | Rice et al. |
| 2010/0323387 | A1 | 12/2010 | Bailey et al. |
| 2010/0330643 | A1 | 12/2010 | Kilian et al. |
| 2011/0015415 | A1 | 1/2011 | Singh et al. |
| 2011/0059495 | A1 | 3/2011 | Bailey et al. |
| 2011/0091977 | A1 | 4/2011 | Kilian et al. |
| 2012/0190115 | A1 | 7/2012 | Kilian et al. |
| 2013/0102040 | A1 | 4/2013 | Radakovits et al. |
| 2013/0131330 | A1 | 5/2013 | Kilian et al. |

FOREIGN PATENT DOCUMENTS

| | | | |
|---|---|---|---|
| WO | WO2009/149470 | A1 | 12/2009 |
| WO | WO2010/011335 | A1 | 1/2010 |
| WO | WO2011/011463 | A2 | 1/2011 |
| WO | WO2011/049995 | A1 | 4/2011 |

OTHER PUBLICATIONS

Wendland et al., Curr. Gen. (2003) 44:115-123.*

Kindle et al., J. Cell. Biol., (1989), 109:2589-2601.*

Molnar et al. Highly specific gene silencing by artificial microRNAs in the unicellular alga *Chlamydomonas reinhardtii*. Plant Jour. ePub Jan. 17, 2009 vol. 58 No. 1 pp. 157-164. Especially abstract.

Chen et al. Conditional Production of a Functional Fish Growth Hormonal in the Transgenic Line of *Nannochloropsis oculata* (Eustigmatophyceae). J. Phycol. Jun. 2008 vol. 44 No. 3 pp. 768-776. Especially abstract.

Abe et al. AG610981, Musmusculus molossinus DNA 2004.

Kopczynski et al.CO268749, *Drosophila melanogaster* cDNA clone EK092604 2004.

Csogor et al. "Light distribution in a novel photobioreactor—modeling for optimization" Journal of Applied Phycology, vol. 13, p. 325-333, May 2001, Entire document, especially: abstract; p. 110, col. 1-2 [online]. Retrieved from the Internet on [Oct. 5, 2010]. Retrieved from: <URL: http://www.springerlink.com/content/p77j66g3j2133522/fulltext.pdf.

Endo et al. "Inactivation of Blasticidin S by *Bacillus cereus* II. Isolation and Characterization of a Plasmid, pBSR 8, from *Bacillus cereus*," The Journal of Antibiotics 41 (2): 271-2589-2601.

Genbank Accession No. U71602 (*Nannochloropsis* sp. Violaxnthin/chlorophyll a binding preotein precursor (NAVCP) mRNA), 1996.

Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).

Janssen, M. "Photosynthetic efficiency of *Dunaliella* tertiolecta under short light/dark cycles" Enzyme and Microbial Technology, 29, 2001, pp. 298-305.

Janssen et al. "Enclosed outdoor photobioreactors: light regime, photosynthetic efficiency, scale-up, and future prospects" Biotechnology and Bioengineering, vol. 81, No. 2, p. 193-210, Jan. 20, 2003, Entire document, especially: Fig 4, p. 198 [online]. Retrieved from the Internet on [Oct. 5, 2010]. Retrieved from: <URL: http://onlinelibrary.wiley.com/doi/10.1002bit.10468/pdf.

Nelson et al. Targeted Disruption of the NIT8 Gene in Chlamydomonas reinhardtii. Mol. Cell Bio. Oct. 1995. vol. 15, No. 10, pp. 5762-5769. Especially abstract and pp. 5763 left col. Para. 2.

Roessler et al. (Generic Engineering Approaches for Enhanced Production of Biodiesel Fuel from Microalgae, ACS Symposium Series; American Chemical Society, 1994; p. 255-270).

Saenz, M.E. "Effects of Technical Grade and a Commercial Formulation of Glyphosate on Algal Population Growth" Bulletin of Environmental Contamination Toxicology, 1997, pp. 638-644.

Shi et al. Analysis of expressed sequence tags from the marine microalga *Nannochloropsis* oculata (eustigmatophyceae) J Phycol v 44, p. 99-102 (2008).

Strzepek et al., "Photosynthetic architecture differs in coastal and oceanie diatoms" Nature vol. 431, p. 689-692, Oct. 7, 2004, Entire document, especially: abstract, p. 689, col. 2; p. 691, Table 1 [online] Retrieved from the Internet on [Oct. 5, 2010]. Retrieved from: URL:http://www.nature.com/nature/journal/v431/n7009/pdf/nature02954.pdf.

Sukenik et al (Journal of Psychology. Jun. 2000; 36(3): 563-570).

Thiel et al. Transformation of a Filamentous Cyanobacterium by Electroporation. Journal of Bacteriology. Oct. 1989, vol. 171, No. 10, pp. 5743-5746, especially p. 5743, abstract, p. 5744, left column, first paragraph, Fig 1.

Zittelli et al. "Mass cultivation of Nannochloropsis sp. In annular reactors" Journal of Applied Phycology vol. 15, p. 107-113, Mar. 2003. Entire document, especially: abstract; p. 110, col. 1-2 [online]. Retrieved from the Internet on [Oct. 5, 2010]. Retrieved from: <URL: http://www.springerlink.com/content/v77772k1mp081775/fulltext.pdf.

Santin-Montanya, I. "Optimal Growth of Dunaliella Primolecta in Axenic Conditions to Assay Herbicides," Chemosphere, 66, Elsevier 2006, p. 1315-1322.

Felix, R. "Use of the cell wall-less alga Dunaliella bioculata in herbicide screening tests," Annals of Applied Biology, 113, 1988, pp. 55-60.

Christy et al., "Effects of Glyphosate on Growth of Chlorella," Weed Science, vol. 29, Issue 1, Jan. 1981, pp. 5-7.

Kureshy et al., "Effect of Ozone Treatment on Cultures of Nannochloropsis oculata, Isochrysis galbana, and Chaetoceros gracilis," Journal of the World Aquaculture Society, 1999, 30(4), pp. 473-480.

Krienitz et al., "Nannochloropsis limnetica (Eustigmatophyceae), a new species of picoplankton from freshwater," Phycologia, 2000, vol. 39, No. 3, Abstract.

Lee et al., "Isolation and Characterization of a Xanthophyll Aberrant Mutant of the Green Alga Nannochloropsis oculata," Marine Biotechnology, 2006, vol. 8, pp. 238-245.

Sukenik et al., "Regulation of Fatty Acid Composition by Irradiance Level in the Eustigmatophyte Nannochloropsis," Journal of Phycol., 1989, vol. 25, pp. 686-692.

Rocha et al., "Growth Aspects of the Marine Microalga Nannochlorpsis gaditana," Biomolecular Engineering, 2003, vol. 20, pp. 237-242.

Macintyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.

Dunahay et al, "Manipulation of Microalgal Lipid Production Using Genetic Engineering," Applied Biochemistry and Biotechnology, 1996, vol. 57/58/.

Witkowski et al., "Conversion of a B-Ketoacyl Synthase to a Malonyl Decarboxylase by Replacement of the ActiveSite Cysteine with Glutamine," Biochemistry, 1999, vol. 38, 11643-11650.

(56) References Cited

OTHER PUBLICATIONS

Kisselev, "Polypeptide Release Factors in Prokaryotes and Eukaryotes: Same Function, Different Structure," Structure, vol. 10, Jan. 2002.
Whisstock et al., "Predication of protein function from protein sequence and structure," Q. Rev. Biophysics, 2003, vol. 36, pp. 307-340.
Broun et al., "Catalytic Plasticity of Fatty Acid Modification Enzymes Underlying Chemical Diversity of Plant Lipids," Science, vol. 282, 1998.
Wishart et al., "A Single Mutation Converts a Novel Phosphotyrosine Binding Domain into a Dual-specificity Phosphatase," J. Biol. Chem. 1995, vol. 270(45), pp. 26782-26785.
Geng et al, "Construction of a System for the Stable Expression of Foreign Genes in Dunaliella Salina," Acta Botanica Sinica 46(3): 342-346, 2004.
Chen et al., "Highly Efficient Expression of Rabbit Neutrophil Peptide-1 gene in Chlorella Ellipsoidea Cells," Current Genetics 39(5-6): 365-370, 2001.
Suga et al., "Control by Osmolarity and Electric Field Strength of Electro-Induced Gene Transfer and Protein Release in Fission Yeast Cells," Journal of Electrostatics 64(12): 796-801, 2006.
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.
Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Colunbia Orinoquia, ISSN: 0121-3709 ed: Unillanosv. 7, fasc. 1-2, pp. 70-100, 2004.
Technical Card: Glyphosate, Document filed for the Pesticide Action Network and the Alternatives Thereof, for Latin America (RAP-AL)- Communications and Administration Office, Apr. 2008.
Department of Environment, Housing and Territorial Development Ministry, Resolution (1009), published Jun. 17, 2008.
International Search Report and Written Opinion of the International Searching Authority mailed Oct. 30, 2009 for Application No. PCT/US2009/046656, filed Jun. 8, 2009.
International Search Report and Written Opinion of the International Searching Authority mailed Aug. 12, 2009 for Application No. PCT/US2009/003819, filed Jun. 25 2009.
International Search Report and Written Opinion of the International Searching Authority mailed Dec. 20, 2010 for Application No. PCT/US2010/053265, filed Oct. 19, 2010.
Extended European Search Report mailed Mar. 19, 2013 in European Patent Application 10825551.4, filed on Oct. 19, 2010.
Minoda et al., "Improvement of Culture Conditions and Evidence for Nuclear Transformation by Homologous Recombination in a Red Alga, Cyanidioschyzon merolae 10D," Plant and Cell Physiology, vol. 45, No. 6, Jun. 2004, pp. 667-671.
Hallmann et al., "Gene Replacement by Homologous Recombination in the Multicellular Green Alga, Volvox carteri," Proceedings of the National Academy of Sciences in the United States of America, vol. 94, No. 14, 1997, pp. 7469-7474.
Kilian et al., "High-efficiency homologous recombination in the oil-producing alga Nannochloropsis sp.," Proceedings of the National Academy of Sciences of the United States of America, vol. 108, No. 52, Dec. 2001, pp. 21265-21269.
Extended European Search Report mailed Oct. 19, 2011 in European Patent Application 09759628.2, filed on Jun. 8, 2009.
Hallmann, "Algal Transgenics and Biotechnology," Transgenic Plant Journal, Global Science Books Ltd., GB, vol. 1, No. 1, Jan. 2007, pp. 81-98.
International Search Report and Written Opinion of the International Searching Authority mailed Oct. 20, 2010 for Application No. PCT/US2010/001754, filed Jun. 16, 2010.
International Search Report and Written Opinion of the International Searching Authority mailed Sep. 9, 2009 for Application No. PCT/US2009/046650, filed Jun. 8, 2009.
International Search Report and Written Opinion of the International Searching Authority mailed Jun. 15, 2011 for Application No. PCT/US2010/042666, filed Jul. 20, 2010.
Pollock, "High Carbon Dioxide Requiring Mutants of Chlamydomonas Reinhardtll," Created Dec. 2003, [online, retrieved Oct. 14, 2010] <http://etd.Isu.edu/docs/available/etd-0828103-114026/unrestricted/Pollock_dis.pdf>.
Drocourt: GenBank Accession No: X52869.1, created Jan. 3, 1995.
Pan: GenBank Accession No: EE109892.1, created Jun. 23, 2008.
Pan: GenBank Accession No: EE109907, created Jun. 23, 2008.
Henriquez et al.: GenBank Accession No: Q07CY9, created Oct. 31, 2006.
International Search Report and Written Opinion of the International Searching Authority mailed Oct. 16, 2012 for Application No. PCT/US2012/035633, filed Apr. 27, 2012.
Yu et al., "Construction and characterization of a normalized cDNA library of Nannochloropsis oculata (Eustigmatophyceae)," Chinese Journal of Oceanology and Limnology, vol. 28, No. 4, pp. 802-807, 2010.
Lumbreras et al., "Efficient Foreign Gene Expression in Chlamydomonas Reinhardtii Mediated by an Endogenous Intron," The Plant Journal, vol. 14, No. 4 Jan. 1, 1998, pp. 441-447, XP001150496, ISSN: 0960-7412, DOI: 10.1046/j.1365-313X.1998.00145.X.
Rose A.B., "Intron-Mediated Regulation of Gene Expression," Current Topics in Microbiology and Immunology vol. 326, Jan. 1, 2008, pp. 277-290, XP009145370, ISSN: 0070-217X.
Rose A.B., "The Effect of Intron Location on Intron-Mediated Enhancement of Gene Expression in Arabidopsis," The Plant Journal, vol. 40, No. 5, Dec. 1, 2004, pp. 744-751, XP55029911, ISSN: 0960-7412, DOI:10.1111/j.1365-313X.2004.02247.
Endo et al. "Inactivation of Blasticidin S by Bacillus Cereus II. Isolation and Characterization of a Plasmid, pBSR 8, from Bacillus Cereus," The Journal of Antibiotics 41 (2): 271-2589-2601, 1988.
Schiedlmeier et al., "Nuclear Transformation of Volvox Carteri" Proceedings of the National Academy of Sciences USA 91(11): 5080-5084 (May 1994).

* cited by examiner

```
AGTCGTAGCAGCAGGAATCGACAATATGTGTTCTCGTTTCTGC
ATACGTCGACTCTGGACAGCTATGACTGACCCGACTCTGACCACACTTCATGACCCACCC
ACCACACAACGAGGGCAGGTGCCGCAGCAGCTTTAGCACGTTGCTCCTCTACATGGCCTT
TAAACTCTCACCACAGGTGCCTACGGCGCCTGAGCCGGTCCGTGCCACCAGTACAGACGC
GCGAGACGATGACACGGCAGACAAGTGGGTTCAGCGCCTGCCAGGCATGATCCGCCTGAC
GGGTCGCCACCCGTTTAACGCCGAGCCGCACACCAAGGAGCTGGTCGACGCTGGCTTCAT
TACCCCCGCCGCCATGCACTATGTGCGGTAAGTCCTTCTTTTCTGGGTCGGCCAATCCAG
TTCGTGTCTCTCATCATCTTTCTAAACTACACCATCACCTACAGCAACCACGGCCCAGTA
CCCAAGCTTGCCTGGGATGACCACCGCATAACCGTGACCGGCCTTGGCGTAGCTGAGCCC     } 310
CAGGTTTTGTCAATGGACGAACTGGTCGCCCTGCCCAATCGAACCCTGCCCGTCACTCTT
GTCTGCGCCGGCAATCGCCGCAAGGAGGTTAACGTCACCCGGCAGAGCAAGGGCTTCAGC
TGGGGCTCCGGTGCAGTGAGCACCTCCATTTGGACGGGCGTGCCCCTGCACGTGCTTCTG
CGCCACTGTGGCGTTGACCCCGATGCGTTAGAGCCCGGACAATACTGGGTCAACTTCGAC
GGGCCTGACGGGGAGCTGCCCAAGGGCATTTATGGCACGAGTATCCCCCTCCTCAAGGTA
AGCATTCGGGCATATATTTATGCATGCTTGTGCTCATTGTCATCCAGTTATGACAAAACT
ATCCATCTTTTCTTTTTTCCAGGCGCTGGATCCAGCACAGGATGTGCTTGTGGCCTTCAA
GCAGAACCACGAGCGCCTCCTCCCCGACCACGGCTTCCCTGTCCGCCTCATTATTCCA

GG
TACACAATCAAACATACACATACACACCCATACACGCACATACATACATGAACCACAGCC
ATATTACTCACTTTCCTTTTTATCTCCTCTACTTGCAGGGTACATAGGGGACGGATGAT    } 315
CAAATGGCTTACTCGCATCACTATCAGCCGCCAAGAGTCGCAGTCCTTTTACCACTTCCA
CGACAATCGCGTCCTGCCCTCGTCGGTGGACCAAGAGCGCGCGGATAATGAGGGCTGGTG

GCGCAAGCCTGAGTACATCATCAACGACCTCAACCTTAACTCGGCCATCACCCATCCGGT
ACGTACTCGTGTCCGCGGGCCTCAGCTGGGATTACGAAAGTTTACAAACGTGCAAGCTCG
CCGCTTATACTGCTGTTCGTCATTTTCCCTGCCAGACTCACGACGAGGAGATCCCGCTGA
AGAAAGGCACTTACAAACTCCAAGGCTACGCCTACTGTGGTGGCGGCCGGCAAGTGCAAC
GCATGGAGGTCTCCCTCGACGATGGCAAGGTAGGAAGTATCACCTTGTCGCGGTTTTCAC
ACTGCTATCATTGACTCAATCGACATTTACACACCCATTCCGACTACGCACCACGAGTAG
AGCTGGGAACTAGCTCAGCTGAGCAGTGAGGAGTACCCAACTGAACACGGCCGCTTCTGG
TGCTGGCGTATTTGGAATCTTGATGTCGACATCCTACGTCTGGTGAGTGCAGCTTGAGAA
CGAGCGAGAAACGTCTGTGTTCCATCACGCTCTCATATATACAATCCCTCCCTCTCTCAT    } 320
AGGTGGGCTGTACGAATGTCGCCTGTCGTGCATGGGACAACTCGCAGAACACACAGCCTC
GAGACTTGACGTGGAACGTCCTAGGCAGTGAGTATTTCGTTTCCTCTCTTCTAGAGATAC
TTTTATTCCATCCATCTCTATCTTTACCTGTGTCTATGAGAGTAAGAGTAATCGTCACAC
CTTATTCATACCCCTGAACTCCCCTTTCCACCCCTCCCTTCCCTACCCACAGTGATGAAC
AACAGCTGGTTCCGGCTTACAACCGCGGTTAGTCTCAACGATCGCCAGCAGCCTGTCGTC
CGCATCAAGCACCCGGCGCCCATTGCTCCTGGTGGGTGGATGGAGGCAGGGGCCGACGAG
ACTGTAAATGTACAGGCCAAGACAACGGGTACCGGTAGCGGACGGTCACACGTGGAAGAC
AAGTCTGTCCCATCGATAGCGCAGCGTAAGGATTTGTCCGTCAT
```

FIG. 3 (SEQ. ID. NO. 1)

```
AGTCGTAGCAGCAGGAATCGACAATATGTGTTCTCGTTTCTGC
ATACGTCGACTCTGGACAGCTATGACTGACCCGACTCTGACCACACTTCATGACCCACCC
ACCACACAACGAGGGCAGGTGCCGCAGCAGCTTTAGCACGTTGCTCCTCTACATGGCCTT
TAAACTCTCACCACAGGTGCCTACGGCGCCTGAGCCGGTCCGTGCCACCAGTACAGACGC
GCGAGACGATGACACGGCAGACAAGTGGGTTCAGCGCCTGCCAGGCATGATCCGCCTGAC
GGGTCGCCACCCGTTTAACGCCGAGCCGCACACCAAGGAGCTGGTCGACGCTGGCTTCAT
TACCCCCGCCGCCATGCACTATGTGCGGTAAGTCCTTCTTTTCTGGGTCGGCCAATCCAG
TTCGTGTCTCTCATCATCTTTCTAAACTACACCATCACCTACAGCAACCACGGCCCAGTA
CCCAAGCTTGCCTGGGATGACCACCGCATAACCGTGACCGGCCTTGGCGTAGCTGAGCCC
CAGGTTTTGTCAATGGACGAACTGGTCGCCCTGCCCAATCGAACCCTGCCCGTCACTCTT
GTCTGCGCCGGCAATCGCCGCAAGGAGGTTAACGTCACCCGGCAGAGCAAGGGCTTCAGC
TGGGGCTCCGGTGCAGTGAGCACCTCCATTTGGACGGGCGTGCCCCTGCACGTGCTTCTG
CGCCACTGTGGCGTTGACCCCGATCGGTTAGAGCCCGGACAATACTGGGTCAACTTCGAC
GGGCCTGACGGGGAGCTGCCCAAGGGCATTTATGGCACGAGTATCCCCCTCCTCAAGGTA
AGCATTCGGGCATATATTTATGCATGCTTGTGCTCATTGTCATCCAGTTATGACAAAACT
ATCCATCTTTTCTTTTTTCCAGGCGCTGGATCCAGCACAGGATGTGCTTGTGGCCTTCAA
GCAGAACCACGAGCGCCTCCTCCCCGACCACGGCTTCCCTGTCCGCCTTCATTATTCCA
```
} 310'

```
CTGATCTTGTCCATCTCGTGTGCCACGGGTGGCAAGAAAAGCTGGGGGAAAAGACAGGATCAA
CACGGCAAAGAGAATCAAGTTCTCTTTGTGACGTCTTTTGGGCGGTTTGACGTGTCGAACTCTTC
TTTTTCTTCAATTAATCCTCACACTTTTGTTTTCTCCATCACATGTAGTGAAAGAGGTACACATGA
GAACTAACGGATTCGTGATTTAAACAACTTTTTCAAAGACAACACACAAGCCTTTCCCCCGGCTC
CACTCTCAATGCTCAACAGATCTGTTTCTCTTCTACTCGCCCTCCTTTCACACGCTTGCGTTCGTTG
TTCTTGTTTTCCCCTCTCTACCTTCCTCTCACTATAAACAAAGAAAATTTTATGTAAAATAAGGGT
GACAAAAGAAGAACCAGGGAGAAAAGAAAATGACGGGGGTAGGAAAGGACTACAGAGAAAAA
CATGATGCAGGAATTCAACACTCTCATATCAAGCAATCAGCACAAACAAACGAAGACAGCTACG
GGAGAAAGGCCTTATTTCTCTTCCGGTAGGTTAAGAAGGGATGGACAATCTCTCGCGCCAACACT
GAGTGCTGCGGCTGCTACTGCTGCTGCTACTGCTACTACCACTGGCTCTTCCACAGAAGCTTAGTC
CTGCTCCTCGGCCACGAAGTGCACGCAGTTGCCGGCCGGGTCGCGCAGGGCGAACTCCCGCCCCC
ACGGCTGCTCGCCGATCTCGGTCATGGCCGGCCCGGAGGCGTCCCGGAAGTTCGTGGACACGACCT
CCGACCACTCGGCGTACAGCTCGTCCAGGCCGCGCACCCACCCAGGCCAGGGTGTTGTCCGGCA
CCACCTGGTCCTGGACCGCGCTGATGAACAGGGTCACGTCGTCCCGGACCACACCGGCGAAGTCGT
CCTCCACGAAGTCCGGGAGAACCCGAGCCGGTCGGTCCAGAACTCGACCGCTCCGGCGACGTCGC
GCGCGGTGAGCACCGGAACGGCACTGGTCAACTTGGCCATACTTAAGAAGTGGTGGTGGTGGTGCT
GCTGCTGTAGAGGATATGGCATCGGGGGTGGGACACGAGCGGGATGTAAGTGTTGCGATGTTTTGA
GGGGTTTCGTCGGGTATGGTGCGAGTCGTGTGAAAGATGTGGAGCACGTGTGGAAAAGGGCAAGAG
AACTGGGCAGAACGTATCTAGGTTTGAAAGCACTCTTCATACTTGATCGCTGGATACGCAACTCAAG
GGAAAGGTCTCTCGAAAGAACAAGAGCGAGAGCCCAGGCTCCTAGAAGGAAGAGCAAGGGGAGGT
CTGTCCATGTCCAATCAGGTAAAGCACACAAAGAGCGAAGTACAAGGTATCAGCTCTAGCAACTTG
GTCAACTAGCTGGGTTTTCTTGTGACAGGGAAAGACTGTTGAAGATAGATCAGGGGGCACTTATGG
GCTCTCAAGAGGGTTGAGCTGAGCCTGTTCCCTGCTCCGCTTTGTCCGACGACAGAAGGCTTTGCGGG
TCTTGCCCTCGGGATCCTTACTGCAAGGTTGAGGCGTTGAGCAGACCCCATGGGAGGTCGTTGAGGCT
TTCGGCACTAAGACAAGATAGGCAAGATGCCCCAATGTCCTGTTACCAACTGGGGTGTGGAAGCACGC
CTGGAGCCTCAAGGGCTCGTTGATAAGGGGATGAAATCGTCCCGGCGAGCAAATCCTGGTTGACCTC
GCAGGATCGTTGAAAAGCAGGAGGCACGTTCGGCGCGAGCCGGTCTGTTGCAGACGCGTGCCATCTT
GTTCCGTCTTGCTTGCGCAAGCCTGAGTACATCATCAA
```
} 410

```
GCGCAAGCCTGAGTACATCATCAACGACCTCAACCTTAACTCGGCCATCACCCATCCGGT
ACGTACTCGTGTCCGCGGGCCTCAGCTGGGATTACGAAAGTTTACAAACGTGCAAGCTCG
CCGCTTATACTGCTGTTCGTCATTTTCCCTGCCAGACTCACGACGAGGAGATCCCGCTGA
AGAAAGGCACTTACAAACTCCAAGGCTACGCCTACTGTGGTGGCGGCCGGCAAGTGCAAC
GCATGGAGGTCTCCCTCGACGATGGCAAGGTAGGAAGTATCACCTTGTCGCGGTTTTCAC
ACTGCTATCATTGACTCAATCGACATTTACACACCCATTCCGACTACGCACCACGAGTAG
AGCTGGGAACTAGCTCAGCTGAGCAGTGAGGAGTACCCAACTGAACACGGCGCTTCTGG
TGCTGGCGTATTTGGAATCTTGATGTCGACATCCTACGTCTGGTGAGTGCAGCTTGAGAA
CGAGCGAGAAACGTCTGTGTTCCATCACGCTCTCATATATACAATCCCTCCCTCTCTCAT
AGGTGGGCTGTACGAATGTCGCCTGTCGTGCATGGGACAACTCGCAGAACACACAGCCTC
GACACTTGACGTGGAACGTCCTAGGCAGTGAGTATTTCCTCCTCTTCTAGAGATAC
TTTTATTCCATCCATCTCTATCTTTACCTGTGTCTATGAGAGTAAGAGTAATCGTCACAC
CTTATTCATACCCCTGAACTCCCCTTTCCACCCCTCCCTTCCCTACCCACAGTGATGAAC
AACAGCTGGTTCCGGCTTACAACCGCGGTTAGTCTCAACGATCGCCAGCAGCCTGTCGTC
CGCATCAAGCACCCGGCGCCCATTGCTCCTGGTGGGTGGATGGAGGCAGGGGCCGACGAG
ACTGTAAATGTACAGGCCAAGACAACGGGTACCGGTAGCGGACGGTCACACGTGGAAGAC
AAGTCTGTCCCATCGATAGCGCAGCGTAAGGATTTGTCCGTCAT
```
} 320'

FIG. 4 (SEQ. ID. NO. 2)

HOMOLOGOUS RECOMBINATION IN AN ALGAL NUCLEAR GENOME

CROSS-REFERENCE TO RELATED APPLICATIONS

The present application is related to U.S. Non-Provisional patent application Ser. No. 12/480,635 filed on Jun. 8, 2009, titled "VCP-Based Vectors for Algal Cell Transformation," which is hereby incorporated by reference.

The present application is related to U.S. Non-Provisional patent application Ser. No. 12/480,611 filed on Jun. 8, 2009, titled "Transformation of Algal Cells," which is hereby incorporated by reference.

REFERENCE TO SEQUENCE LISTINGS

The present application is filed with sequence listing(s) attached hereto and incorporated by reference.

BACKGROUND OF THE INVENTION

1. Field of the Invention

This invention relates to molecular biology, and more specifically, to the expression of exogenous DNA elements in algal cells.

2. Description of Related Art

Manipulating the DNA of a cell may confer upon the cell new abilities. For example, a transformed cell (i.e., a cell that has taken-up exogenous DNA) may be more robust than the wild-type cell. For many so-called model biological systems (i.e., well-studied organisms), the DNA elements for transformation have been developed. For other organisms, of which less is known, transformation is a major milestone that must be achieved to facilitate genetic engineering. Complicating this challenge is the need for efficient, non-random transformation of these organisms. Accordingly, there is a need for homologous recombination in an algal nuclear genome.

SUMMARY OF THE INVENTION

Provided herein are exemplary transformation methods for introducing deoxyribonucleic acid (DNA) into the nucleus of an algal cell. A transformation construct may be prepared, with the transformation construct having a first sequence of DNA similar to a corresponding first sequence of nuclear DNA, a second sequence of DNA similar to a corresponding second sequence of the nuclear DNA, and a sequence of DNA of interest inserted between the first and second sequences of DNA of the transformation construct. A target sequence of DNA inserted between the first and second corresponding sequences of the nuclear DNA may be transformed, resulting in replacement of the target sequence of DNA with the sequence of DNA of interest. In further exemplary embodiments, the sequence of DNA of interest may comprise an antibiotic resistance marker, a promoter sequence and an antibiotic resistance marker, or a gene for nutrient assimilation or biosynthesis of a metabolite. A phenotypic characteristic of the algal cell may be changed or new characteristics may be imparted to the algal cell.

Also provided is an exemplary transformation construct, the transformation construct having a first sequence of DNA similar to a corresponding first sequence of nuclear DNA of an algal cell, a second sequence of DNA similar to a corresponding second sequence of nuclear DNA of the algal cell, and a sequence of DNA of interest inserted between the first and second sequences of the transformation construct. According to a further exemplary embodiment, the sequence of DNA of interest may further comprise DNA to compromise or destroy wild-type functioning of a gene for nutrient assimilation or biosynthesis of a metabolite.

BRIEF DESCRIPTION OF THE DRAWINGS

FIG. 3 shows an exemplary DNA sequence (SEQ. ID. NO. 1), which includes at least a portion of a nitrate reductase gene.

FIG. 4 shows an exemplary transformation construct (SEQ. ID. NO. 2), which incorporates nitrate reductase DNA sequences for the flanks of the transformation construct.

DETAILED DESCRIPTION OF THE INVENTION

Figure 1:
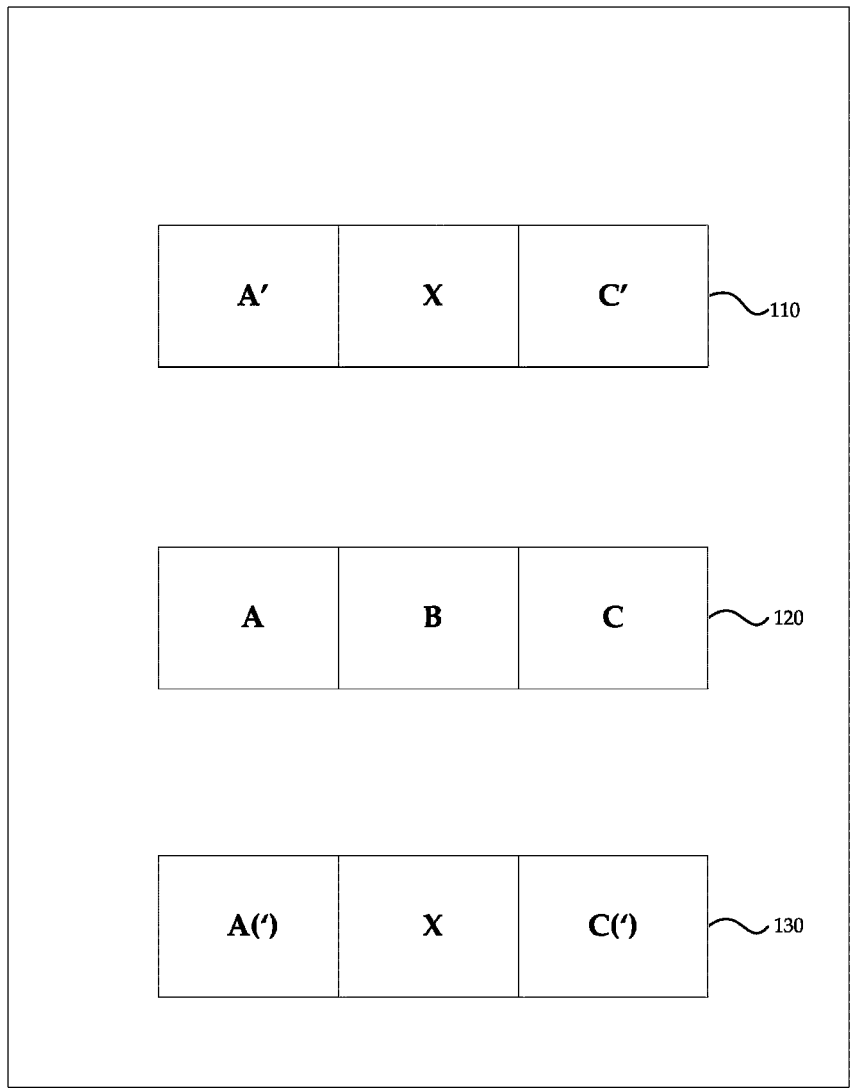
FIG. 1 is a diagram showing how exemplary deoxyribonucleic acid (DNA) sequences may be utilized for introducing DNA into the nucleus of an algal cell, according to one exemplary embodiment.

FIG. 1 is a diagram showing how exemplary deoxyribonucleic acid (DNA) sequences may be utilized for introducing DNA into the nucleus of an algal cell, according to one exemplary embodiment. Shown in FIG. 1 is a transformation construct 110, algal nuclear DNA 120, and transformed algal nuclear DNA 130.

The transformation construct 110 comprises a first sequence of DNA A' that is similar in length and sequence to a corresponding first sequence of algal nuclear DNA A, as found in the algal nuclear DNA 120. The transformation construct 110 comprises a second sequence of DNA C' that is similar in length and sequence to a corresponding second sequence of the nuclear DNA C as found in the algal nuclear DNA 120. The transformation construct 110 further comprises a sequence of DNA of interest X that is inserted between the first A' and second C' sequences of DNA of the transformation construct 110.

In one exemplary method for introducing DNA into the nucleus of an algal cell, a transformation construct such as exemplary transformation construct 110 is prepared. The transformation construct 110 may then be used to transform a target sequence of DNA B inserted between the first A and second C sequences of the nuclear DNA 120, resulting in replacement of the target sequence of DNA B with the sequence of DNA of interest X.

According to various exemplary embodiments, the first A' and/or the second C' sequences of DNA similar to the corresponding respective first A and/or the second C sequences of the nuclear DNA 120 may be of any length in base pairs (bps), ranging from approximately 0 bps to approximately 10,000 (bps), or longer. Additionally, the first sequence of DNA A' may or may not have a length in base pairs equal to a length in base pairs of the second sequence of DNA C'.

In various exemplary embodiments, the target sequence of DNA B inserted between the first A and second C sequences of the nuclear DNA 120 may be of any length in base pairs, ranging from approximately 0 bps to approximately 10,000 (bps), or longer.

According to some exemplary embodiments, the sequence of DNA of interest X may separate the first A' and second C' sequences of the transformation construct 110 by as few as approximately 0 (bps) to as many as approximately 10,000

(bps). The sequence of DNA of interest X may comprise various sequences, such as a regulatory or promoter sequence (uni-directional or bi-directional), an antibiotic resistance marker, or may comprise a promoter sequence and an antibiotic resistance marker. In other exemplary embodiments, the sequence of DNA of interest X may comprise a gene for nutrient assimilation or biosynthesis of a metabolite. For instance, the sequence of DNA of interest X may comprise a gene coding for nitrate reductase or nitrite reductase.

In various exemplary embodiments, the sequence of DNA of interest X may or may not encode at least a portion of a polypeptide. In some cases, the sequence of DNA of interest X may only be transcribed, however not translated as a polypeptide. In other embodiments, the sequence of DNA of interest X may encode a peptide that is added to a peptide encoded by either the first A or the second C sequence of the nuclear DNA 120. The sequence of DNA of interest X may also encode a non-coding regulatory DNA sequence. In various exemplary embodiments, the sequence of DNA of interest X may not be similar in length to the target sequence of DNA B on the nuclear DNA 120. For instance, the sequence of DNA of interest X may be approximately 0 (bps) in length, resulting in deletion or near deletion of the target sequence of DNA B, as may be observed in the transformed algal nuclear DNA 130.

According to some exemplary embodiments, the transformation construct 110 may be used to transform a target sequence of DNA B inserted between the first A and second C sequences of the nuclear DNA 120, resulting in replacement of the target sequence of DNA B with the sequence of DNA of interest X. The nuclear DNA 120 may be at least a portion of a genome from the algal genus *Nannochloropsis*. Further, the genome of the algal genus *Nannochloropsis* may be a haploid genome. The transformation methodologies described herein may be used to change a phenotypic characteristic of an algal cell to impart new characteristics to the algal cell. For instance, the replacement of the target sequence of DNA B with the sequence of DNA of interest X may be at least a partial replacement, resulting in a partial decrease in gene function of the target sequence of DNA. In other embodiments, the sequence of DNA of interest X may comprise DNA to compromise or destroy wild-type functioning of the target gene B gene, which is otherwise needed for nutrient assimilation or biosynthesis of a metabolite. Conversely, the sequence of DNA of interest X may be used to transform the compromised or destroyed wild-type functioning of the gene for nutrient assimilation or biosynthesis back to wild-type functioning. For instance, the sequence of DNA of interest X may transform an auxotrophic algal cell, resulting in assimilation or biosynthesis of a metabolite. Such transformants may be selected via cultivation in a liquid or solid media that does not include the metabolite required for growth of the transformed auxotrophic algal cell.

Figure 2:
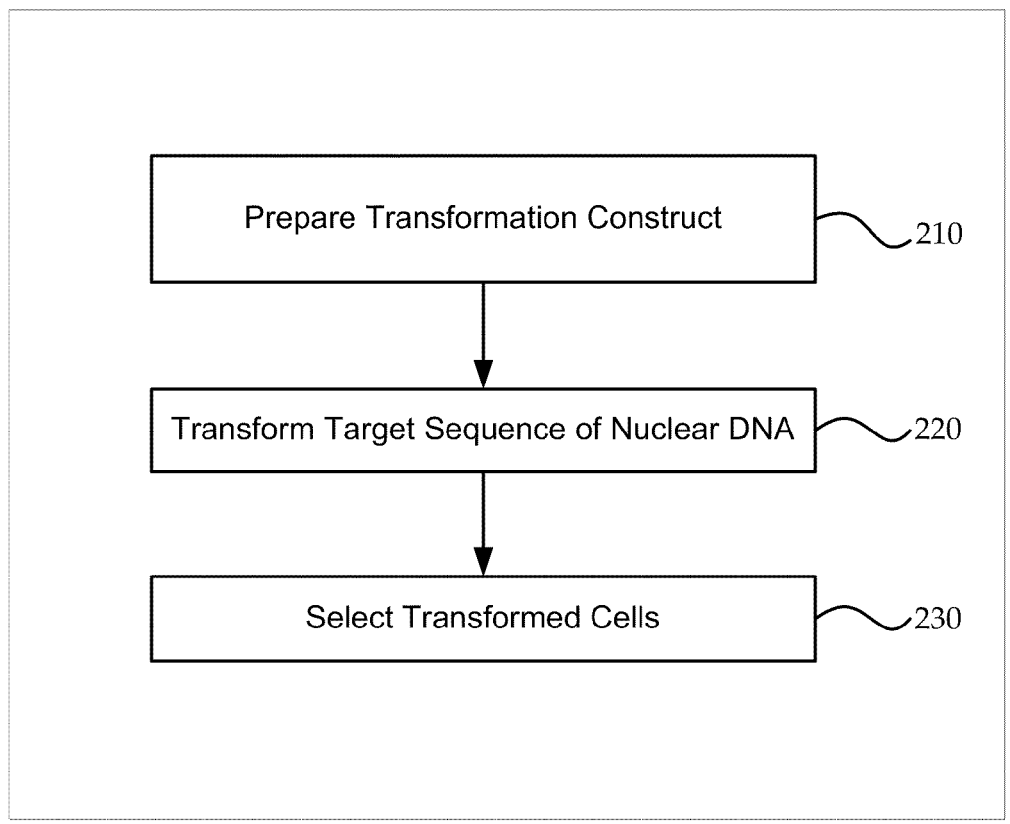
FIG. 2 is a flow chart showing an exemplary method for homologous recombination in an algal nuclear genome.

FIG. 2 is a flow chart showing an exemplary method for homologous recombination in an algal nuclear genome.

At step 210, a transformation construct is prepared. In one exemplary embodiment, the transformation construct 110 (FIG. 1) comprises a first sequence of DNA A' that is similar to a corresponding first sequence of algal nuclear DNA A as found in the algal nuclear DNA 120 (FIG. 1). The transformation construct 110 may also comprise a second sequence of DNA C' that is similar to a corresponding second sequence of the nuclear DNA C as found in the algal nuclear DNA 120. The transformation construct 110 may have a sequence of DNA of interest X inserted between the first A' and second C' sequences of DNA of the transformation construct 110.

At step 220, a target sequence of nuclear DNA is transformed. According to various exemplary embodiments, the transformation construct 110 is used to transform a target sequence of DNA B inserted between the first A and second C sequences of the nuclear DNA 120, resulting in replacement of the target sequence of DNA B with the sequence of DNA of interest X.

At step 230, transformed cells are selected. For instance, the sequence of DNA of interest X may transform an auxotrophic algal cell, resulting in assimilation or biosynthesis of a metabolite. Such transformants may be selected via cultivation in a liquid or solid media that does not include the metabolite required for growth of the transformed auxotrophic algal cell.

Example

In order to test the possibility of homologous recombination in *Nannochloropsis*, the inventors created a transformation construct which utilized a selectable marker (a bleomycin gene) flanked by a left and a right nitrate reductase DNA sequence.

FIG. 3 shows an exemplary DNA sequence (SEQ. ID. NO. 1), which includes at least a portion of a nitrate reductase gene.

Referring to FIG. 3, a left nitrate reductase DNA sequence is designated 310, and a right nitrate reductase DNA sequence is designated 320. As will be described herein, a DNA sequence 315 between flanks 310 and 320 will be displaced from the endogenous nitrate reductase gene with DNA sequences from the transformation construct.

FIG. 4 shows an exemplary transformation construct (SEQ. ID. NO. 2), which incorporates the nitrate reductase DNA sequences used to create the flanks of the transformation construct. FIG. 4 shows the left nitrate reductase DNA sequence 310', a selection cassette NT7 410, and the right nitrate reductase DNA sequence 320'. The selection cassette NT7 410 comprises a Violaxanthin-chlorophyll a binding protein ("Vcp") 3' UTR, a bleomycin resistance sequence, and a Vcp promoter sequence. The Vcp promoter and the Vcp 3'UTR DNA sequences were obtained from 2 different Vcp gene clusters, as described in U.S. Non-Provisional patent application Ser. No. 12/480,635 filed on Jun. 8, 2009, titled "VCP-Based Vectors for Algal Cell Transformation. The NT7-cassette comprising the Vcp promoter, bleomycin resistance sequence, and Vcp 3' UTR were inserted in an antiparallel fashion relative to the left nitrate reductase flank 310' and the right nitrate reductase flank 320'.

Design.

Primers Used.

Homologous recombination of Vcp ble UTR into NR, reverse direction and deletion of part of one exon P311 NR LEFT for (SEQ. ID. NO. 3) AGTCGTAGCAG-CAGGAATCGACAA.

P312 NR LEFT rev (SEQ. ID. NO. 4) GGCACAC-GAGATGGACAAGATCAGTGGAATAAT-GAGGCGGACAG GGAA.

P313 NR RIGHT for (SEQ. ID. NO. 5) GTGCCATCT-TGTTCCGTCTTGCTTGCGCAAGCCTGAG-TACATCATCA A.

P314 NR RIGHT rev (SEQ. ID. NO. 6) ATGACGGA-CAAATCCTTACGCTGC.

P215 NT7 comp for (SEQ. ID. NO. 7) AAGCAAGACG-GAACAAGATGGCAC.

P119 PL38 3UTR BACK (SEQ. ID. NO. 8) CTGATCT-TGTCCATCTCGTGTGCC.

PCRs were performed with Takara Taq to generate NR flanks and insertion cassette:

P311×P312 on gDNA for Left flank LF (1 kB).

P313×P314 on gDNA for Right flank RF (1.04 kB).

(NOTE: both flanks contain fusion areas to NT7 derived from primer 312 and 313).

P215×P119 on NT7 for Insertion construct IC (1.817 kB).

All PCR products were then gel purified.

The LF, IC and RF fragments were linked with the following PCRs:

ALL 100 μl PCR RXNs 170 ng of LF+170 ng IC were used in fusion PCR with P311×P215 (2.817 kB)LF-IC.

170 ng of RF+170 ng IC were used in fusion PCR with P119×P314 (2.821 kB)RF-IC.

Fragments were gel purified and used for last PCR.

170 ng LF-IC+170 ng RF-IC with P311×P314.

3.8 kB DNA Fragment recovered from gel and directly used for transformation.

Transformation.

200 ng DNA fragment (see above) were used in the previously described transformation protocol.

Differences: cells were grown in NH4CL-containing F2 media (2 mM NH4Cl instead of nitrate). Recovery after transformation before plating was also done in 2 mM NH4Cl medium.

Cells were plated on F2 (zeocine-containing) plates with 2 mM NH4CL (instead of 2 mM NO3-). All media in 50% salinity compared to seawater.

Selection.

200 colonies were picked, resuspended in 100 μl nitrogen-deficient F2 media and spotted on Square plates (F2 media) with different nitrogen sources:

No Nitrogen 2 mM No2-

2 mM NO3-

2 mM NH4Cl

The overwhelming majority of these colonies could not grow on nitrate (turned yellowish indicating nitrogen starvation; nitrate reductase knock-out mutants cannot grow on nitrate as the sole nitrogen source), but all clones grew equally well on nitrite and ammonium-chloride plates. Further, appearance of those clones suppressed in growth on nitrate was indistinguishable from cells (transformed or untransformed) grown on nitrogen-deficient (no nitrogen) plates indicating that the growth retardation of mutants on nitrate is due to an inability to use nitrate as a nitrogen source. Growth retardation on agar plates containing nitrate as the sole nitrogen source was never observed with wild types nor with mutants obtained from nitrate reductase unrelated transformation, indicating that the clones were inactivated within the nitrate reductase gene.

Results.

Figure 5:
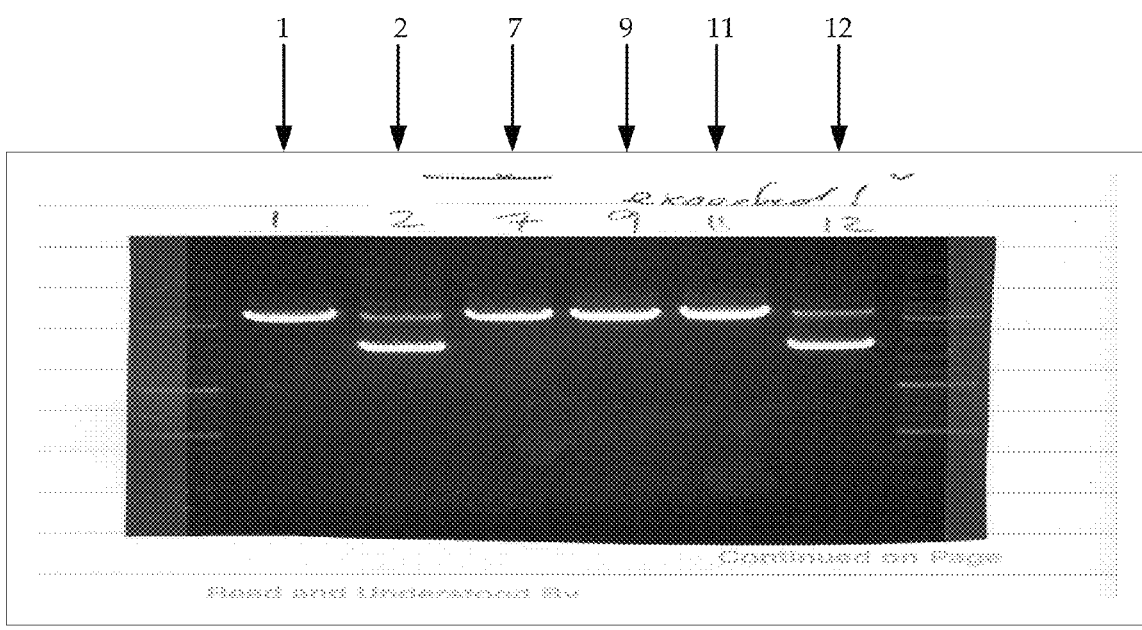
FIG. 5 is a gel showing the molecular genetic analysis of several transformants.

FIG. 5 is a gel showing the molecular genetic analysis of several transformants.

192 clones were analyzed. 176 of these were apparently nitrate reductase deficient via visual screening. Colonies were also analyzed via PCR. The gel in FIG. 5 shows the molecular genetic analysis of several transformants (designated 1, 2, 7, 9, 11 and 12). Clones 2 and 12 have been identified to grow on nitrate as a sole nitrogen source, while clones 1, 7, 9 and 11 could not, indicating a disruption of the nitrate reductase gene.

The primer used for genetic analysis via PCR would yield a smaller DNA fragment for the wild-type gene and a larger DNA fragment for a mutant gene which contains the large selection marker insertion.

The lanes labeled 1, 7, 9 and 11 show only one band that corresponds to the nitrate reductase locus with the expected insert. Lanes labeled 2 and 12 show two bands—the smaller band is the endogenous nitrate reductase gene, and the larger band is the transformation construct fragment, which is inserted somewhere else in the genome but not within the nitrate reductase locus.

Sequencing.

Sequencing was employed to verify if there were errors introduced after recombination. 6 clones were analyzed via PCR, and the flanking regions including the flank ends (5' end of left flank and 3' end of right flank) were sequenced. No error could be found. The entire locus has also been amplified out of transformants (nitrate reductase interrupted by ble gene cassette) and successfully used for repeated transformations of wild-type.

The inventors were also successful using a wild-type nitrate reductase fragment as a selection marker to rescue a knock out mutant by homologous recombination: the wild-type fragment patched over the insertion site of the ble gene within the nitrate reductase gene and replaced it.

Only those clones, in which the nitrate reductase gene was rescued by homologous recombination, could grow on nitrate as the sole nitrogen source.

While various embodiments have been described above, it should be understood that they have been presented by way of example only, and not limitation. Thus, the breadth and scope of a preferred embodiment should not be limited by any of the above-described exemplary embodiments.

What is claimed is:

1. A transformation method for introducing deoxyribonucleic acid (DNA) into the nucleus of an algal cell, the method comprising:

preparing a transformation construct, the transformation construct having a first sequence of DNA similar to a corresponding first sequence of nuclear DNA, the transformation construct having a second sequence of DNA similar to a corresponding second sequence of the nuclear DNA, the transformation construct having a sequence of DNA of interest inserted between the first and second sequences of DNA of the transformation construct, transforming a target sequence of DNA inserted between the first and second corresponding sequences of the nuclear DNA, resulting in replacement of the target sequence of DNA with the sequence of DNA of interest, wherein the algal cell is of algal genus *Nannochloropsis*.

2. The method of claim 1, wherein the sequence of DNA of interest separates the first and second sequences of DNA similar to the corresponding respective first and second sequence of the nuclear DNA by approximately 4.5 kb.

3. The method of claim 1, wherein either the first or second sequence of DNA similar to the corresponding respective first or second sequence of the nuclear DNA comprises approximately 1000 base pairs (bps).

4. The method of claim 1, wherein either the first or second sequence of DNA similar to the corresponding respective first or second sequence of the nuclear DNA comprises approximately less than 1000 bps.

5. The method of claim 1, wherein either the first or second sequence of DNA similar to the corresponding respective first or second sequence of the nuclear DNA comprises approximately greater than 1000 bps.

6. The method of claim 1, wherein either the first or second sequence of DNA similar to the corresponding respective first or second sequence of the nuclear DNA comprises approximately greater than 10,000 bps.

7. The method of claim 1, wherein the sequence of DNA of interest further comprises a regulatory or promoter sequence.

8. The method of claim 7, wherein the promoter is uni-directional or bi-directional.

9. The method of claim 1, wherein the sequence of DNA of interest further comprises a promoter sequence and an antibiotic resistance marker.

10. The method of claim 1, wherein the sequence of DNA of interest further comprises a gene for nutrient assimilation or biosynthesis of a metabolite.

11. The method of claim 10, wherein the gene codes for nitrate reductase or nitrite reductase.

12. The method of claim 1, wherein the sequence of DNA of interest is approximately 0 bps, resulting in deletion or near deletion of the target sequence of DNA.

13. The method of claim 1, wherein the sequence of DNA of interest is transcribed but does not encode a polypeptide.

14. The method of claim 1, wherein the sequence of DNA of interest encodes a peptide that is added to a peptide encoded by either the first or the second sequence of nuclear DNA.

15. The method of claim 1, wherein the sequence of DNA of interest encodes a non-coding regulatory DNA sequence.

16. The method of claim 1, wherein the algal cell of the algal genus *Nannochloropsis* is used for the production of biofuels.

17. The method of claim 1, wherein the algal cell is haploid.

18. The method of claim 1, the method further comprising:
   changing a phenotypic characteristic of the algal cell or imparting new characteristics to the algal cell.

19. The method of claim 1, wherein the first sequence of DNA similar to the corresponding first sequence of the nuclear DNA has a first length in base pairs which does not equal a second length in base pairs of the second sequence of DNA similar to the corresponding second sequence of the nuclear DNA.

20. The method of claim 1, wherein the target sequence of DNA is less than 1 kb.

\* \* \* \* \*

SEQUENCE LISTING

<160> NUMBER OF SEQ ID NOS: 6

<210> SEQ ID NO 1
<211> LENGTH: 24
<212> TYPE: DNA
<213> ORGANISM: Algae

<400> SEQUENCE: 1
agtcgtagca gcaggaatcg acaa                                      24

<210> SEQ ID NO 2
<211> LENGTH: 48
<212> TYPE: DNA
<213> ORGANISM: Algae

```
<400> SEQUENCE: 2
ggcacacgag atggacaaga tcagtggaat aatgaggcgg acagggaa            48

<210> SEQ ID NO 3
<211> LENGTH: 48
<212> TYPE: DNA
<213> ORGANISM: Algae

<400> SEQUENCE: 3
gtgccatctt gttccgtctt gcttgcgcaa gcctgagtac atcatcaa            48

<210> SEQ ID NO 4
<211> LENGTH: 24
<212> TYPE: DNA
<213> ORGANISM: Algae

<400> SEQUENCE: 4
atgacggaca aatccttacg ctgc                                      24

<210> SEQ ID NO 5
<211> LENGTH: 24
<212> TYPE: DNA
<213> ORGANISM: Algae

<400> SEQUENCE: 5
aagcaagacg gaacaagatg gcac                                      24

<210> SEQ ID NO 6
<211> LENGTH: 24
<212> TYPE: DNA
<213> ORGANISM: Algae

<400> SEQUENCE: 6
ctgatcttgt ccatctcgtg tgcc                                      24
```